(12) United States Patent
Takahashi et al.

(10) Patent No.: US 6,511,419 B2
(45) Date of Patent: Jan. 28, 2003

(54) ENDOSCOPE TIP PART WITH NO SWELL AT OUTER SKIN FIXING PART

(75) Inventors: Kazuaki Takahashi, Saitama (JP); Tadashi Ando, Saitama (JP)

(73) Assignee: Fuji Photo Optical Co., Ltd., Saitama (JP)

(*) Notice: Subject to any disclaimer, the term of this patent is extended or adjusted under 35 U.S.C. 154(b) by 0 days.

(21) Appl. No.: 09/956,858

(22) Filed: Sep. 21, 2001

(65) Prior Publication Data

US 2002/0040179 A1 Apr. 4, 2002

(30) Foreign Application Priority Data

Sep. 29, 2000 (JP) ......................... 2000-298659

(51) Int. Cl.[7] ................................................ A61B 1/04
(52) U.S. Cl. ....................................... 600/129; 600/130
(58) Field of Search ................................. 600/129, 130, 600/170, 171, 176, 177; 398/76; 356/241.5

(56) References Cited

U.S. PATENT DOCUMENTS 5,894,369 A * 4/1999 Akiba et al. .................. 348/65

2002/0028983 A1 * 3/2002 Ando et al. ................. 600/127

FOREIGN PATENT DOCUMENTS

| JP | 61-219922 | * | 9/1986 | ............ A61B/1/04 |
| JP | 6-70882 | * | 3/1994 | ............ A61B/1/04 |

* cited by examiner

*Primary Examiner*—John Mulcahy
(74) *Attorney, Agent, or Firm*—Snider & Associates; Ronald R. Snider

(57) ABSTRACT

In an endoscope tip part in which a lens barrel is arranged and fixed to a mounting hole of a support body of the endoscope tip part and to this lens barrel, and an optical member such as an optical filter or a prism is connected by an optical part holding fixture, a part of an endoscope outer peripheral side of the optical part holding fixture is cut off, and to this notch part, the mounting hole is extended out like an extending part, and a step part on an outside of this support member is made deep (diameter is reduced). If an end part of an outer skin is bound with a string on this step part with a small diameter and fixed by adhesives, a swell of an outer skin fixing part is eliminated, and an insertion of the endoscope also becomes easy.

3 Claims, 3 Drawing Sheets

ENDOSCOPE TIP PART WITH NO SWELL AT OUTER SKIN FIXING PART

BACKGROUND OF THE INVENTION

This application claims the priority of Japanese Patent Applications No. 2000-298659 filed on Sep. 29, 2000 which is incorporated herein by reference.

1. Field of the Invention

The present invention relates to a structure of an endoscope tip part, and particularly, to the structure of an endoscope tip part whose diameter is decreased for making the insertion into an observed body easy.

2. Description of the Prior Art

In FIG. 5 and FIG. 6, a configuration of a tip part of a conventional endoscope apparatus is shown, and at a tip part 1, a lens barrel 3 of an object optical system, a treating device inserting channel (pipe) 4, or a light guide 5 is arranged in a mounting hole of an internal support body 2. To the above described lens barrel 3, an optical part holding fixture 6 which includes this lens barrel 3 and contains an optical member such as an optical filter is provided, and to this optical part holding fixture 6, a prism 7 is optically connected, and to this prism 7, a CCD (Charge CoupledDevice) (or a CCD package) 8 is bonded.

Then, to the above described support body 2, a cap 9 made of synthetic resin is attached on the tip side thereof, and in the meantime, on the rear end side, a sleeve 10 is connected, and on the outer periphery of these sleeve 10 and support body 2, an outer skin 11 made of rubber is covered. That is, at the outer peripheral part of the above described support body 2, a step part 2A which goes inside from the same position as the outer peripheral position of the sleeve 10 is formed, and the end part of the outer skin 11 arranged at this step part 2A is wound by a string, and on this string winding part 12, adhesives 13 or the like are applied, so that the outer skin 11 is fixed.

Thus, to the tip part 1, the object optical system including the lens barrel 3, the treating device inserting channel 4, and the light guide 5 or the like are arranged at specified positions, and in the meantime, the outer periphery of this tip part 1 is covered by the cap 9 made of synthetic resin and the outer skin 11 made of rubber. Then, by these cap 9 and outer skin 11, the electrical insulation can be ensured between the interior and the exterior in the endoscope.

However, in the case of the above described endoscope tip pat, as shown in FIG. 5, the thickness is thin at part of the step part 2A, and from the point of view of ensuring the strength of the support body 2, it is impossible to make this step part 2A deep, and therefore, the circumferential part of the above described string winding part 12 and adhesives 13 that is the fixing part of the outer skin 11 a little swells as shown in the drawing, and there has been such a problem that the reduction of the diameter of the endoscope tip part 1 is prevented, and that the easiness of insertion thereof is affected.

That is, conventionally, the reduction of the diameter of the tip part (insertion part) 1 has been tried by planning the shape of each internal member and the arrangement thereof, but if the circumferential part of the fixing part of the above described outer skin 11 swells, the diameter is increased as a result by the amount corresponding thereto. Furthermore, the smooth insertion of the tip part 1 is prevented more badly as the difference between this swell part (outer skin fixing part) and the outside diameter of the outer skin 11 becomes larger.

BRIEF SUMMARY OF THE INVENTION

The present invention is achieved in view of the above described problems, and it is an object thereof to provide an endoscope tip part in which the swell of the outer skin fixing part at the tip part is eliminated, and the reduction of the diameter and the easiness of insertion of the endoscope are not prevented.

In order to attain the above described object, the present invention includes: a lens barrel provided to an endoscope tip part; an optical part holding fixture which is fitted on the outer peripheral rear side of the above described lens barrel for connecting an optical member to this lens barrel; a tip part support member having a mounting hole where the above described lens barrel is fitted and arranged; and a recess (for example, a step part or a fixing groove) which is formed like a ring on the outer periphery of this tip part support member and where the end part of the outer skin of the endoscope is arranged to be fixed by fixing means, in which part of the endoscope outer peripheral side of the above described optical part holding fixture is cut off, and to this cut-off part, part of the mounting hole wall of the above described support member is extended out, and the outer peripheral recess of the above described support member is deeply formed (diameter is reduced), and consequently, the swell of the outer skin fixing part is eliminated.

In the above description, it is preferable that the end part of the above described outer skin is bound to the above described recess with a string that is the above described fixing means, and that adhesives are applied on that string winding part.

According to the above described configuration, the step part for fixing the outer skin of the support member can be made deep by the notch of the optical part holding fixture, that is, the diameter can be reduced, and the outer skin end part can be arranged at this step part with a reduced diameter, and therefore, even in the case where this outer skin is fixed by string winding and adhesives are applied, it is possible for the swell at this part to be eliminated or to be made extremely small.

DETAILED DESCRIPTION OF THE PREFERRED EMBODIMENT

Figure 1:
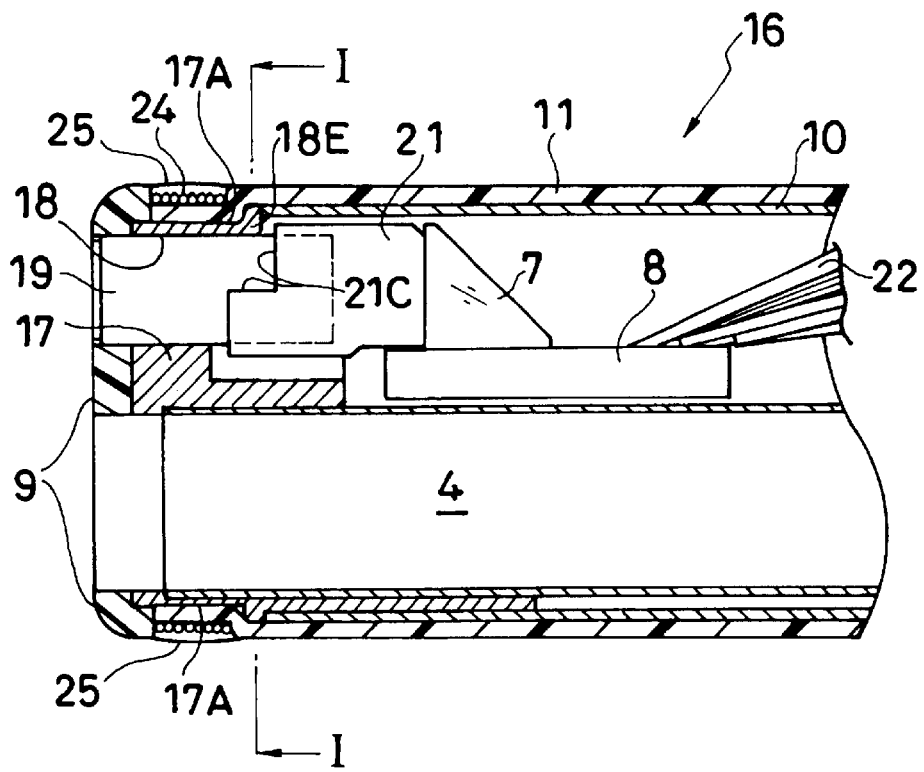
FIG. 1 is a side cross sectional view of an endoscope tip part that is an embodiment of the present invention.
Figure 2:
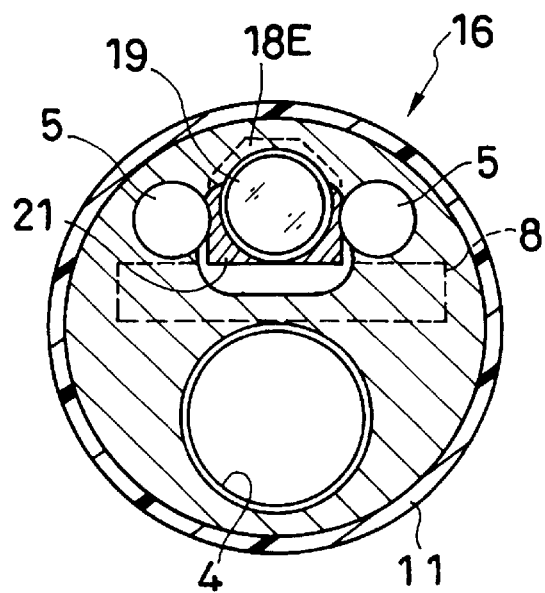
FIG. 2 is a cross sectional view of a line I—I of the endoscope tip part in FIG. 1.
Figure 3A:
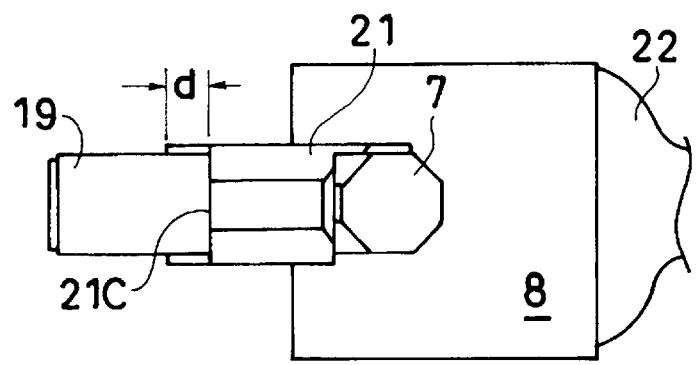
FIG. 3A is a top view of a part of an optical system member and a CCD provided to the endoscope tip part in FIG. 1.
Figure 3C:
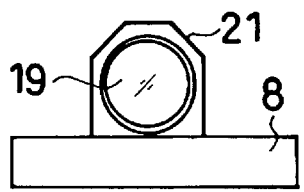
FIG. 3C is a front view of the optical system member and the CCD in FIG. 3A.
Figure 3B:
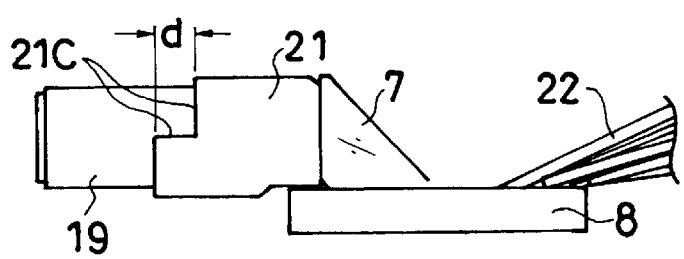
FIG. 3B is a side view of the optical system member and the CCD in FIG. 3A.
Figure 4:
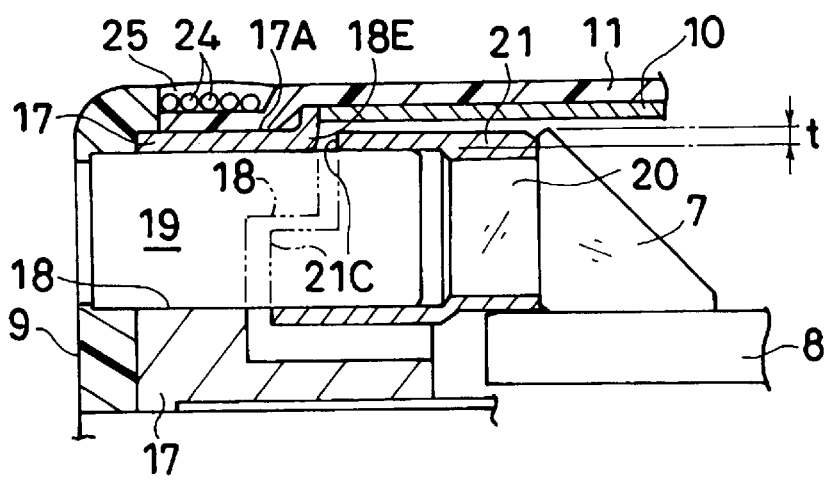
FIG. 4 is an enlarged cross sectional view showing the circumference of the optical system member and the outer skin fixing part of the endoscope tip part in FIG. 1.
Figure 5:
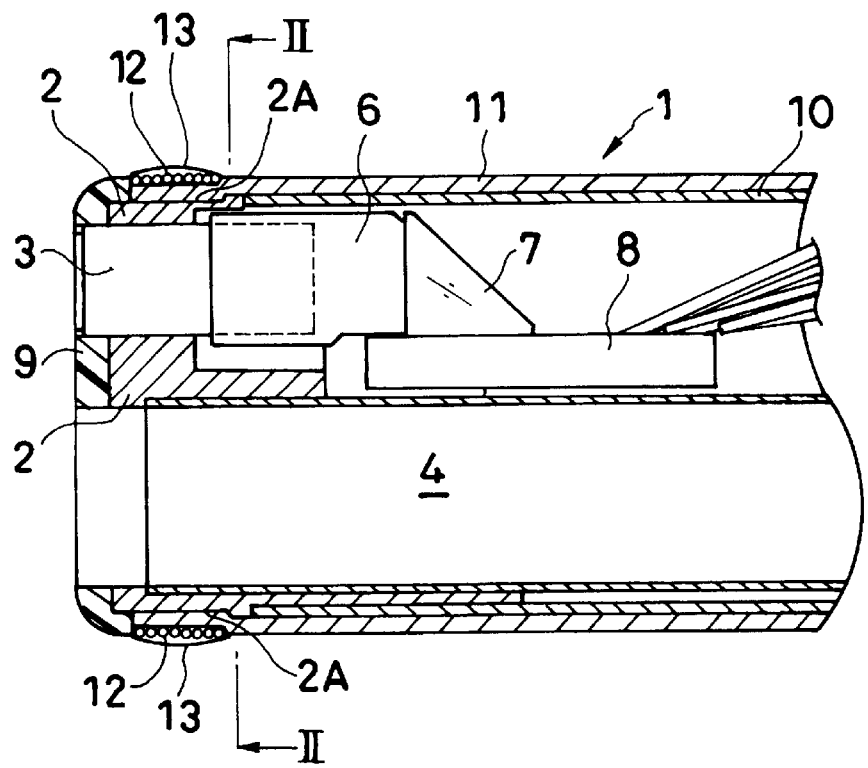
FIG. 5 is a side cross sectional view of a conventional endoscope tip part.
Figure 6:
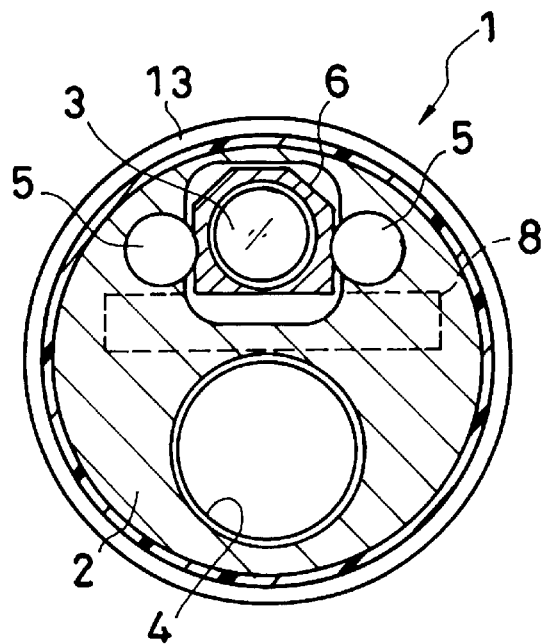
FIG. 6 is a cross sectional view of a line II—II of the endoscope tip part in FIG. 5.

In FIG. 1 to FIG. 4, an endoscope tip part according to an embodiment is shown, and a basic configuration of an endoscope tip part 16 of this endoscope is similar to that in FIG. 5 and FIG. 6. In FIG. 1 and FIG. 2, a lens barrel 19 of an object optical system, a treating device inserting channel 4, and a light guide 5 are arranged in a mounting hole 18 of a support body 17 of the tip part 16, and the above described lens barrel 19 contains, for example, a plurality of object lenses in the interior of a cylindrical holding member.

To this lens barrel 19, as shown in the detailed drawings of FIG. 3 and FIG. 4, an optical part holding fixture 21 which is fitted to the outer periphery of the above described lens barrel 19 and where an optical member 20 such as an optical filter is contained and arranged is provided, and to this optical part holding fixture 21, a CCD (or a package in which a CCD is packaged) 8 that is a solid image pick up element is attached through a prism 7. Furthermore, the output signal of this CCD 8 is supplied to a signal processing part by a signal line 22.

Then, in the case of the above described optical part holding fixture 21 of the present embodiment, a notch part 21C is provided on the tip side of the upper half in the drawing positioned on the outer peripheral side of the endoscope. That is, as shown in FIG. 3A and FIG. 3B, a cylindrical part of 180 degrees (which may be a range of less than this 180 degrees) on the upper side of the optical part holding fixture 21 is cut by a length d from the tip side, and a notch part 21C is provided.

Furthermore, in the space opened by this notch part 21C, as is clear at the time of comparing FIG. 1 with FIG. 5 of the prior art, the upper part (endoscope outer peripheral side part) of the mounting hole 18 of the above described support member 17 is extended out to the rear side more than that of the prior art, and an extending part 18E is provided. Furthermore, a diameter of the step part 17A of the outer periphery of the support body 17 including this extending part 18E is formed smaller than that of the prior art. That is, to the support body 17, a sleeve 10 that is an exterior material is attached, and the step part 17A is formed to be deep toward a center of the endoscope from the outer peripheral position of these support body 17 and sleeve 10.

Then, to the above described support body 17, a cap 9 made of synthetic resin is attached on the tip side thereof, and in the meantime, on the outer periphery of the above described sleeve 10 and support body 17, an outer skin made of rubber (angle rubber) 11 is covered, and fixed. In the case of the present embodiment, in the step part 17A formed deeply in the above described support body 17, the end part of the outer skin 11 is arranged, and a string winding part 24 made by binding and winding the end part of this outer skin 11 with a string is provided, and to the step part 17A having this string winding part 24, adhesives 25 are applied.

According to such an embodiment, the attachment and the fixing to the specified position of each member in the tip part 16 are performed by the support body 17, and in the case of the optical system member, the lens barrel 19, the optical member 20, the optical part holding fixture 21, the prism 7, and the CCD 8 are also attached by fixing the lens barrel 19 in the mounting hole 18 of the support body 17. In this case, the above described optical part holding fixture 21 has a function to optically connect the optical member 20 and the prism 7 to the lens barrel 19.

Then, in the case of the above described support body 17, it is possible to reduce the diameter of the step part 17A thereof making up the outer skin fixing part by the thickness t of the optical part holding fixture 21, and it becomes possible to eliminate (or reduce) the swell of the outer skin fixing part by providing the string winding part 24 and the adhesives 25 while making the outer skin 11 go deeply under this step part 17A.

Furthermore, in the case of the optical part holding fixture 21 of the above described embodiment, part of the upper half is cut off by the notch part 21C, and the lower half is left, and consequently, the reduction of the bonding area with the lens barrel 19 can be prevented as much as possible, and the lowering of the holding and connecting function of the optical part can be restrained.

Furthermore, it is also possible to form a fixing groove formed like a groove in the outer periphery of the support body 17 in place of the above described step part 17A of the present embodiment, and in this case, the depth of the fixing groove should be deep.

As described above, according to the embodiment, the outer skin end part is fixed to the outer peripheral step part of the tip part support member, and in the meantime, at the endoscope tip part connecting the optical member to the lens barrel with the optical part holding fixture, part of the endoscope outer peripheral side of the above described optical part holding fixture is cut off, and to this notch part, the mounting hole of the support member is extended out, and the above described step part of the above described support member is made deep, and therefore, the swell of the outer skin fixing part of the tip part is eliminated. Accordingly, the reduction of the diameter of the endoscope is not prevented, and furthermore, there is also such an advantage that the insertion of the tip part is smoothly performed.

What is claimed is:

1. An endoscope tip part, comprising:

a lens barrel provided to the endoscope tip part;

an optical part holding fixture fitted on an outer peripheral rear side of the lens barrel for connecting an optical member to the lens barrel;

a tip part support member having a mounting hole where the lens barrel is fitted and arranged; and a recess which is formed like a ring on an outer periphery of the tip part support member and where an end part of an outer skin of an endoscope is arranged and fixed by fixing means, wherein part of an endoscope outer peripheral side of the optical part holding fixture is cut off, and to a part which is cut off, part of the wall of a mounting hole of the support member is extended out, and an outer peripheral recess of the support member is deeply formed, and consequently, a swell of an outer skin fixing part is eliminated.

2. The endoscope tip part according to claim 1, wherein the end part of the outer skin is bound to the recess with a string that is the fixing means, and on a string winding part, adhesives are applied.

3. The endoscope tip part according to claim 1, wherein an optical filter is provided as an optical member to be held by the optical holding fixture.

* * * * *